(12) United States Patent
Tang et al.

(10) Patent No.: US 12,134,594 B2
(45) Date of Patent: Nov. 5, 2024

(54) COMPOSITION AND APPLICATION THEREOF AS ANTITUMOR DRUG

(71) Applicant: Guangdong Jianersheng Pharmaceutical Technology Co., Ltd., Guangdong (CN)

(72) Inventors: Xiaojiang Tang, Guangzhou (CN); Xuefeng Ren, Guangzhou (CN); Yichen Ge, Guangzhou (CN); Zhiyong Zhong, Guangzhou (CN); Nina Zheng, Flushing, NY (US)

(73) Assignee: Guangdong Jianersheng Pharmaceutical Technology Co., Ltd., Zhuhai (CN)

( * ) Notice: Subject to any disclaimer, the term of this patent is extended or adjusted under 35 U.S.C. 154(b) by 749 days.

(21) Appl. No.: 17/209,337

(22) Filed: Mar. 23, 2021

(65) Prior Publication Data

US 2021/0276948 A1  Sep. 9, 2021

Related U.S. Application Data

(63) Continuation-in-part of application No. PCT/CN2019/087023, filed on May 15, 2019.

(30) Foreign Application Priority Data

Oct. 11, 2018  (CN) .......................... 201811185272.8

(51) Int. Cl.
 A61P 35/00  (2006.01)
 A61K 33/243  (2019.01)
 C07C 333/04  (2006.01)

(52) U.S. Cl.
 CPC .......... *C07C 333/04* (2013.01); *A61K 33/243* (2019.01); *A61P 35/00* (2018.01)

(58) Field of Classification Search
 None
 See application file for complete search history.

(56) References Cited

U.S. PATENT DOCUMENTS 4,645,661 A    2/1987 Schonbaum
5,002,755 A *  3/1991 Mitchell ............... A61K 33/243
                                              424/649

FOREIGN PATENT DOCUMENTS

CN    1884260 A  * 12/2006

OTHER PUBLICATIONS

Zheng, "The effect of GMDTC in reducing cisplatin-induced toxicities, particularly nephrotoxicity", 2018, State University of Buffalo at New York, Master's Thesis, pp. 1-75 (Year: 2018).*
Byrski et al., "Response to neoadjuvant therapy with cisplatin in BRCA1-positive breast cancer patients", 2009, Breast Cancer Res Treat, 115, pp. 359-363 (Year: 2009).*
Hendrickson et al., "Dithiocarbamates of Cu(I), Cu(II), and Cu(III). An Electrochemical Study", 1976, Inorganic Chemistry, 15, pp. 2115-2119 (Year: 1976).*
Ishida et al., "Enhancing tumor-specific uptake of the anticancer drug cisplatin with a copper chelator", 2010, Cancer Cell, 17, pp. 574-583 (Year: 2010).*
Zhong et al., "Study on the Specific Complexation of GMDTC and Metal Ion", 2018, Chinese Journal of Industrial Hygiene and Occupational Diseases, 36, Abstract Only (Year: 2018).*
Ying Yan et al., Research progress on prevention and treatment of cisplatin nephrotoxicity, Progress in Japanese Medicine, Dec. 31, 2003, pp. 379-381, vol. 24, No. 8.
Satu M. Somani et al., Diethyldithiocarbamate Protection Against Cisplatin Nephrotoxicity: Antioxidant System, Drug and Chemical Toxicology, Dec. 31, 1995, pp. 151-170, vol. 18, No. 2 and 3.
Xiaojiang Tang et al., Mobilization and removing of cadmium from kidney by GMDTC utilizing renal glucose reabsorption pathway, Toxicology and Applied Pharmacology, Jun. 6, 2016, pp. 143-152, vol. 305.
Yuji Wang et al., Development of highly effective three-component cytoprotective adjuncts for cisplatin cancer treatment: synthesis and in vivo evaluation in S180-bearing mice, Metallomics, May 17, 2011, pp. 1212-1217, vol. 3.
Pinliang Zhang et al., Research progress of cisplatin nephrotoxicity prevention, Foreign Medical Sciences (Cancer Section), Apr. 30, 1998, pp. 98-100, vol. 25, No. 2.
International Search Report of PCT Patent Application No. PCT/CN2019/087023 issued on Jul. 2, 2019.

* cited by examiner

*Primary Examiner* — Jeffrey H Murray
*Assistant Examiner* — Madeline E Braun

(57) ABSTRACT

A composition is prepared from a platinum-based antitumor compound and a novel compound, and the novel compound is sodium(S)-2-(dithiocarboxylate ((2S, 3R, 4R, 5R)-2,3,4,5,6-pentahydroxyhexyl)amino)-4-(methylthio)butyrate. The novel compound in the composition could effectively chelate the platinum-based antitumor compound and reduce the various adverse effects exhibited by the platinum-based compound. The dosage of the platinum-based antitumor compound can thus be increased, and the antitumor effect can be optimized. The novel compound itself is low-toxic and it has low chelating activities with essential metals in the human body; it would not impose significant adverse effects on the human body at given doses. The composition and its application as an antitumor drug overcome some technical drawbacks of platinum-based antitumor drugs, namely severe adverse effects and the development of drug resistance during administration.

7 Claims, 13 Drawing Sheets

COMPOSITION AND APPLICATION THEREOF AS ANTITUMOR DRUG

CROSS-REFERENCE TO RELATED APPLICATIONS

This application is a Continuation-In-Part application of PCT Application No. PCT/CN2019/087023 filed on May 15, 2019, which claims priority to Chinese Patent Application No. 201811185272.8 filed on Oct. 11, 2018. The contents of the above-identified applications are incorporated herein by reference in their entirety.

TECHNICAL FIELD

The disclosure belongs to the field of pharmaceutical research and development and particularly relates to a composition and an application thereof as an antitumor drug.

BACKGROUND

Platinum-based antitumor drugs are effective and powerful chemotherapeutic agents. Among platinum-containing antitumor drugs, cisplatin is known as "the penicillin for cancers" and is used in the treatment of various types of cancers. It's estimated that approximately 50% of cancer patients have received platinum-based treatment. Cisplatin combined treatment has become a basic treatment for many cancers.

However, the use and efficacy of platinum-based antitumor drugs, e.g., cisplatin, are restricted by their side effects, in particular, nephrotoxicity and ototoxicity. Cisplatin-induced nephrotoxicity is most severe: the kidney is constantly exposed to cisplatin because cisplatin is mainly excreted from the body by the kidney through both glomerular filtration and tubular secretion. As a result, cisplatin accumulates in the kidney, particularly in proximal tubular cells. In addition, cisplatin's ototoxic potential places cancer patients at risk of hearing loss, with the mechanisms similar to its nephrotoxicity (the cochlea cells accumulate and retain the cisplatin leading to the damage to cellular and molecular components). Due to these side effects, it is prohibited to administer platinum-based antitumor drugs to broader cancer patients and at a higher dose. In practical treatment, platinum-based antitumor drugs are given several cycles at a relatively low dose. Although most cancer patient cells initially respond well to the treatment, the clinical effectiveness declines over time as the cancer cells develop resistance to the platinum-based antitumor drugs.

SUMMARY OF DISCLOSURE

In view of the drawbacks of the prior art, i.e., cisplatin deposition and accumulation in the kidney and the ear, and the development of drug resistance during the administration of platinum-based antitumor drugs, a composition and its application as an antitumor drug combined with platinum-based antitumor drugs have been developed.

The present disclosure provides a composition and an application thereof as an antitumor drug.

In particular, the present disclosure provides a composition comprising a platinum-based antitumor compound and a novel compound with metal chelating activities, wherein the novel compound is sodium (S)-2-(dithiocarboxylate((2S,3R,4R),5R)-2,3,4,5,6-pentahydroxyhexyl)amino)-4-(methylthio)butyrate (also known as GMDTC).

Preferably, the platinum-based antitumor compound is one or more selected from the group consisting of cisplatin, oxaliplatin, and carboplatin.

Preferably, the platinum-based antitumor compound is cisplatin.

Preferably, the composition comprises, in parts by mole, 1-5 parts of the platinum-based antitumor compound and 1-50 parts of the novel compound.

Preferably, the composition comprises, in parts by mole, 1-3 parts of the platinum-based antitumor compound and 1-20 parts of the novel compound.

Preferably, the composition comprises, in parts by mole, 1 part of the platinum-based antitumor compound and 20 parts of the novel compound.

The present disclosure also provides the application of any one of the above compositions as an antitumor drug.

According to the technical solutions provided by the present disclosure, the disclosure has the following beneficial effects:

1. The novel compound in the composition has a high chelating effect on the platinum-based antitumor compound and toxic heavy metals. On the other hand, it does not affect the essential metals (such as calcium, iron, magnesium and zinc) in the body.
2. The compound exhibits high safety performance and no acute toxicity according to experimental data: the acute oral lethal doses (LD50) for rats and mice in animal experiments are greater than 10,000 mg/kg. The composition shows no cytotoxic effect on normal human kidney cells HK2 at an exposure level of 1000 µM over 24 hours; the composition could also reduce apoptosis and cytotoxicity induced by the platinum-based antitumor compound.
3. The composition has significantly improved antitumor efficacy. For example, in a test performed in a mouse model with 4T1 breast carcinoma xenografts, the composition combined treatment could better delay tumor growth and inhibit metastasis than administrating the platinum-based antitumor compound alone.
4. The composition could effectively prevent cisplatin accumulation in the kidney and remove deposited cisplatin from the kidney, thus reducing the nephrotoxicity caused by the platinum-based antitumor compound. These findings are demonstrated by measurements of blood urea nitrogen (BUN) level and creatinine (CRE) level, as well as through tissue examination of renal proximal tubules.
5. Co-treatment using the composition could greatly reduce systemic toxicity in mice and reduce weight loss caused by administrating the platinum-based antitumor compound alone. From the analysis of blood RBC, WBC, PLT and ALT, it can be concluded that blood toxicity and liver toxicity are significantly reduced after co-treatment.

The beneficial effects of the technical solutions provided by the present disclosure are due to the unique structure and component of the novel compounds and achieved through the following mechanism:

1. Actively being absorbed into and excreted out of the cells: GMDTC contains a glucose residue in its structure, therefore it is able to quickly enter the cell through glucose transporters in the cell membrane of many different types of cells.

Removal of deposited cisplatin from kidney, reduced nephrotoxicity: the presence of the glucose residue in GMDTC allows GMDTC to enter renal tubular cells through sodium-glucose cotransporters (SGLT2) present on the surface of the renal tubular lumen. GMDTC can combine with the platinum-based compound through its disulfhydryl residue to form a GMDTC-platinum complex. The GMDTC complex then enters the bloodstream through basal glucose transporters (GLUT2), after which it is filtered by glomeruli and discharged through the urine. Nephrotoxicity is significantly reduced as a result of the excretion of the platinum-based compound.

3. Removal of deposited cisplatin from cochlea cells, reduced ototoxicity: in a similar mechanism as discussed above, the presence of the glucose residue in GMDTC allows GMDTC to enter and out of cochlea cells and remove the formed GMDTC-platinum complex inside the cochlea cells. Ototoxicity is thus significantly reduced as a result of the excretion of the platinum-based compound.

4. The administration of a certain amount of GMDTC is potentially able to increase the level of copper transporter 1 (CTR1), which can in turn accelerate platinum-based antitumor drugs into tumor cells, hence improving the pharmacokinetic properties of the drug.

In summary, the present disclosure provides a composition, which comprises a platinum-based antitumor compound and a novel compound, wherein the novel compound is sodium (S)-2-(dithiocarboxylate ((2S,3R,4R,5R)-2,3,4,5,6-pentahydroxyhexyl)amino)-4-(methylthio)butyrate. The present disclosure also provides an application of the composition as an antitumor drug. Experiments have shown that the novel compound in the composition could effectively chelate the platinum-based antitumor compound and reduce the various adverse effects exhibit by the platinum-based compound when it is used alone. The dosage of the platinum-based antitumor compound can thus be increased, the antitumor effect can be optimized. The novel compound itself is non-toxic and its reaction with essential metals in the human body is low; it would not impose significant adverse effects on the human body at a relatively high dose. The composition and its application as an antitumor drug provided by the present disclosure overcome some technical drawbacks of platinum-based antitumor drugs of the prior art, namely severe adverse effects and the development of drug resistance during administration.

BRIEF DESCRIPTION OF DRAWINGS

To more clearly explain the examples of the present disclosure or the technical solutions in the prior art, the present disclosure is described below with reference to the accompanying drawings. The drawings described below are only some examples of the present disclosure. For those of ordinary skill in the art, other drawings can be obtained based on the drawings provided without creative effort.

DETAILED DESCRIPTION OF EMBODIMENTS

The examples of the present disclosure illustrate a composition and its application as an antitumor drug. The examples aim at overcoming the technical drawbacks of the prior art, including severe adverse reactions and the development of drug resistance during the administration of platinum-based antitumor drugs.

The examples of the present disclosure will be described clearly and thoroughly below. The examples described are only a part of the possible examples of the present disclosure. Based on the examples of the present disclosure, all other examples obtained by the person skilled in the art without creative effort shall fall within the protection scope of the present disclosure.

To explain the present disclosure in more detail, the composition and its application as an antitumor drug provided by the present disclosure will be described in more detail below through the examples.

Example 1

This example illustrates the preparation of antitumor compositions.

Figure 10:
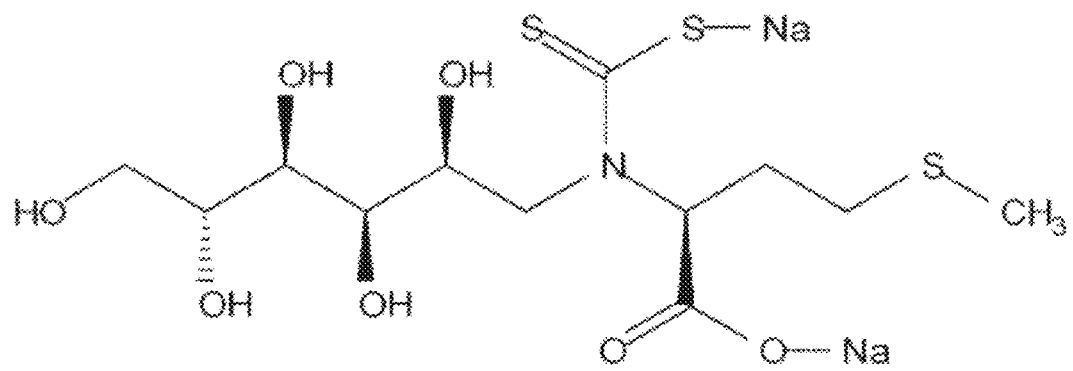
FIG. 10 shows the structural formula of the novel compound in a composition provided by an example of the present disclosure.

Composition 1 is prepared by mixing 1000 μmol of a novel compound (its structural formula is shown in FIG. 10) with 50 μmol of cisplatin in a pharmaceutically acceptable solvent.

Composition 2 is prepared by mixing 1000 μmol of a novel compound with 50 μmol of oxaliplatin in a pharmaceutically acceptable solvent.

Composition 3 is prepared by mixing 1000 μmol of a novel compound with 50 μmol of carboplatin in a pharmaceutically acceptable solvent.

Example 2

This example illustrates the successful formation of a novel compound/platinum-based antitumor compound complex.

This example employs an HPLC assay method. The stationary phase was a C18 column (250 mm*4.6 mm, particle size 5 μm). The gradient mobile phase was as follows: the volume ratio of $H_2O$/acetonitrile was 77 to 23 (+0.1% $H_3PO_4$) from 0 min to 8 min, 68 to 32 (+0.1% $H_3PO_4$) from 8 min to 13 min, 23 to 77 (+0.1% $H_3PO_4$) from 13 min to 16 min, 73 to 23 (+0.1% $H_3PO_4$) from 16 min to 40 min. The flow rate was 1.0 mL/min, sample loading was 10 μL, DAD detector, UV 350 nm complex.

Chemical substances were identified and quantified by ultraviolet-visible (UV/Vis) spectroscopy; UV spectra were obtained by NanodropOne. The results showed that the water-soluble cisplatin has a UV absorption peak at 210 nm, an aqueous solution of the novel compound has two UV absorption peaks at 263 nm and 293 nm.

Figure 1A:
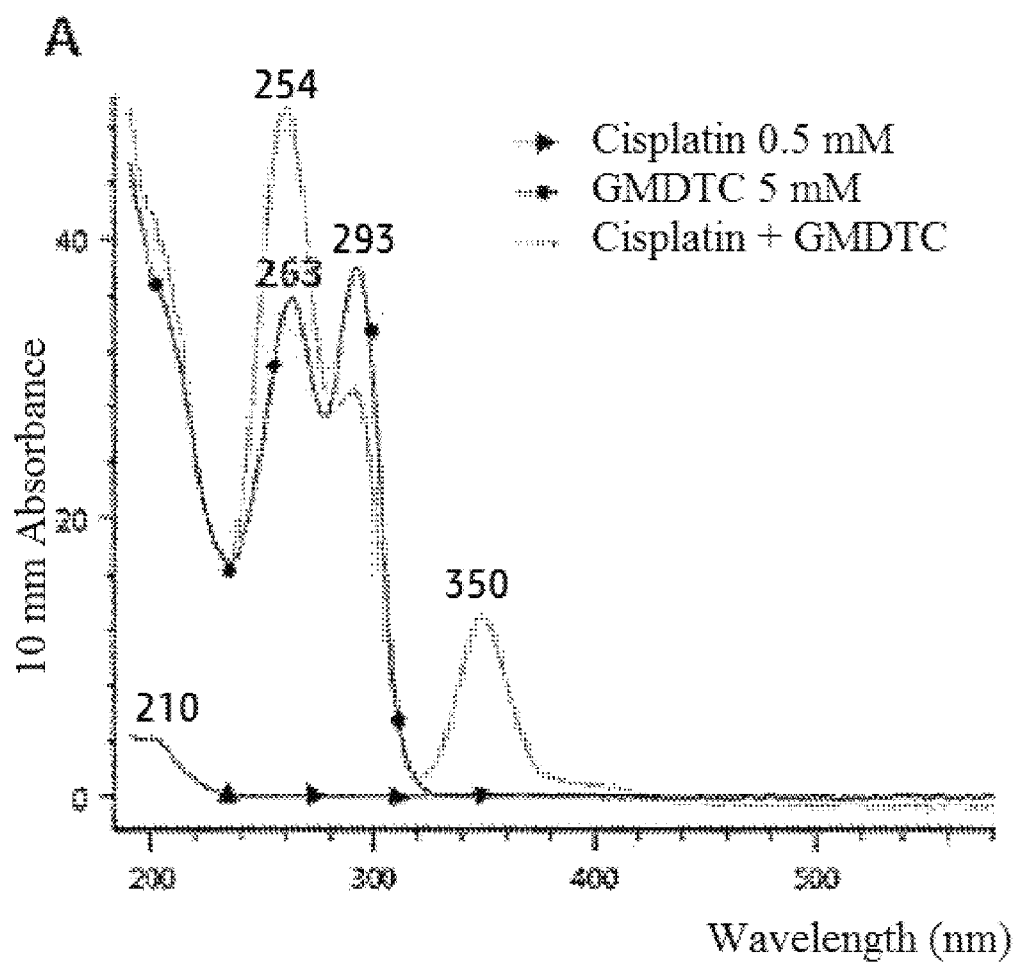
FIG. 1A. shows the UV spectrum of GMDTC, cisplatin, and GMDTC-cisplatin complex measured using Nanodrop. UV spectrum of 0.5 mM Cisplatin (green) (peak UV absorbance at 210 nm), 5 mM GMDTC (orange) (peak UV absorbance at 263 and 293 nm), and GMDTC-Cisplatin complex (yellow) (peak UV absorbance at 254 and 350 nm) according to an example of the present disclosure.
Figure 1B:
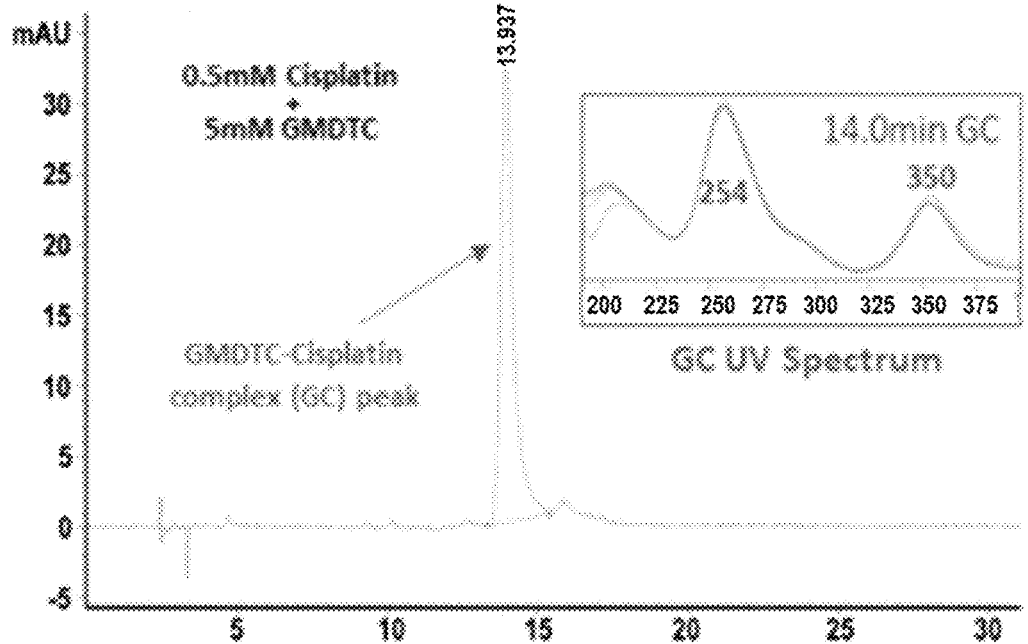
FIG. 1B. shows the UV spectrum of GMDTC-cisplatin complex measured using HPLC according to an example of the present disclosure. The GMDTC-Cisplatin complex elutes from the C18 column at around 14 min and has a similar UV spectrum as Nanodrop.

After mixing cisplatin with the novel compound, the mixture was allowed to react at 4° C. for 24 h to form a new product. It could be seen from FIG. 1A and FIG. 1B that the novel compound could combine with cisplatin to form a novel compound-cisplatin complex.

Example 3

This example examines the in vitro toxicity of the novel compound.

3.1 Cell Culture

The cells involved in this example include a human renal proximal tubular cell line HK2 (ATCCCRL2190), a pig proximal tubular cell line LLC-PK1 (ATCCCL 101) and a mouse breast cancer cell line 4T1 (ATCCCRL2539), which were all purchased from American Type Culture Collection.

LLC-PK1 cells were cultured in Dulbecco modified Eagle's medium (DMEM), HK2 cells were cultured in DMEM/F12 medium, and 4T1 cells were cultured in RPMI 1640 medium. All cell media were supplemented with 10% FBS, 100 units/ml penicillin and 100 units/ml streptomycin. The cell lines were incubated at 37° C. in a 5% CO2 atmosphere and subcultured twice a week. 3.2 In vitro cell viability assay The HK2 cells and the LLC-PK1 cells were treated with trypsin and inoculated in a 100 μL medium in a 96-well plate at a density of 10,000 cells/well. The cells were incubated for 24 h before treatment.

To examine the toxicity of the novel compound, the cells were treated with different doses of the novel compound for 24 h. To examine the ability of the novel compound in reducing the toxicity of the platinum-based antitumor compound (cisplatin as an example), the cells were treated with different doses of the novel compound and 50 μM cisplatin for 24 h. To examine the effect of the novel compound on rescuing the toxicity of cisplatin, the cells were pretreated with 300 μM of cisplatin for 30 min, washed twice with PBS. The medium was then changed, and the cells were treated with different doses of the novel compound for 48 h.

After treatment, cell viability was measured by an MTT assay. 10 μL of a 12 mM MTT (3-(4,5-dimethylthiazol-2-yl)-2,5-diphenyltetrazolium bromide) stock solution was added into each well. After incubation for 4 h at 37° C., the medium was removed; 100 μL of dimethyl sulfoxide (DMSO) was added into each well, and then the plate was incubated for 10 min at 37° C. The plate was shaken in a plate oscillator, and a plate reader (Bio-Tek) was used to measure the absorbance at 570 nm.

3.3 In Vitro FACS Cell Apoptosis Assay

An FITC annexin V/cell apoptosis kit (V13242, Invitrogen) was used to analyze cell apoptosis. HK2 cells and LLC-PK1 cells were cultured in a 6-well plate and then treated with PBS, 50 μM of cisplatin or 50 μM of cisplatin+ 1000 μM of novel compound for 24 h at 37° C.

After treatment, the cells were harvested, washed in cold PBS, and re-suspended in an annexin binding buffer at a density of 1×10⁶ cells/mL; 5 μL of FITC annexin V and 1 μL of 100 μg/mL PI working solution were added to each 100 μL cell suspension. The cells were incubated for 15 min at room temperature.

After incubation, 400 μL of the annexin binding buffer was added and the mixture was mixed gently, the sample was kept on ice at the same time; then, the cell suspension was transferred to a FACS tube. Annexin-V/PI staining was studied in a BDFortessa flow cytometer. Then, fluorescence intensity was measured at 530 nm and >575 nm. Data were analyzed by an FCSExpress6 software (DeNovoSoftware).

3.4. Results 3.4.1 Studying the Toxicity of Novel Compound GMDTC on HK2 Cells and LLC-PK1 Cells HK2 and LLC-PK1 are immortalized proximal renal tubular cell lines. HK2 cells are isolated from human kidneys, LLC-PK1 cells are derived from pig kidneys. These cells were used to study the toxicity of the novel compound or cisplatin in vitro.

Figure 2A:
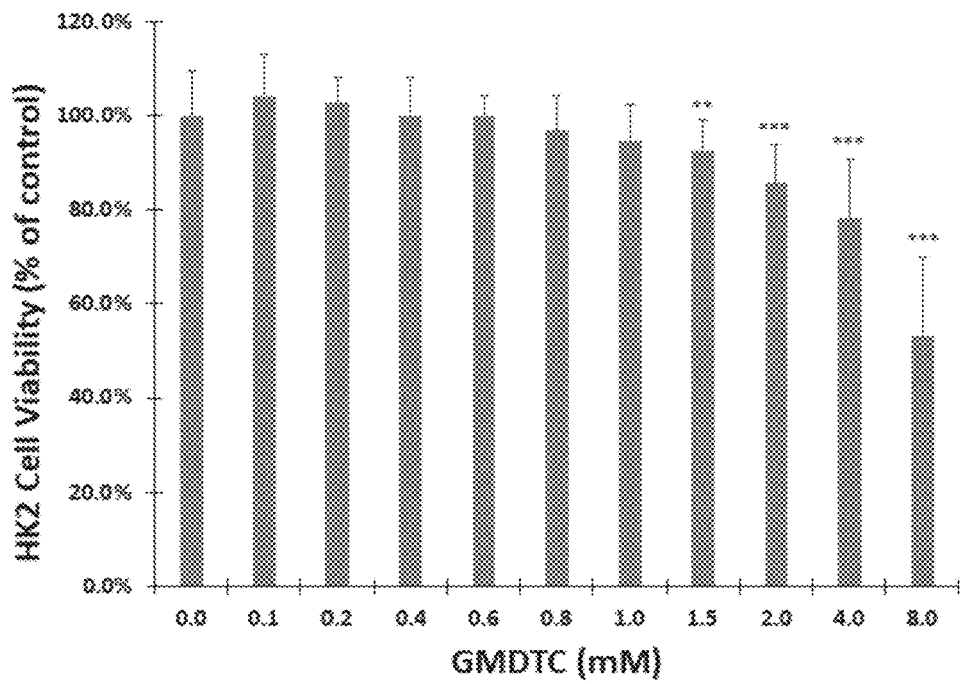
FIG. 2A shows the result of an in vitro cell viability assay of HK2 cells treated with various doses of GMDTC for 24 hours according to an example of the present disclosure.
Figure 2B:
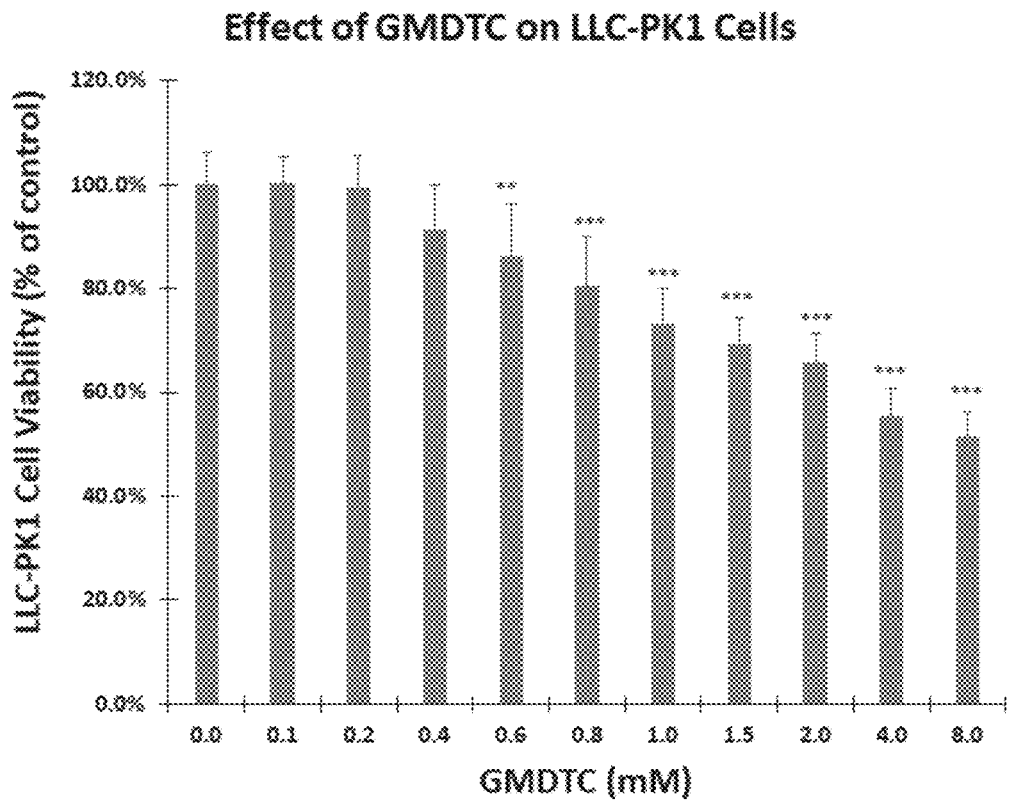
FIG. 2B shows the result of an in vitro cell viability assay of LLC-PK1 cells treated with various doses of GMDTC for 24 hours according to an example of the present disclosure.

HK2 cells and LLC-PK1 cells were treated with different doses of the novel compound for 24 h. Toxicity was studied using an MTT cell viability assay. Compared with a blank control, the impacts of the novel compound on the viability of the HK2 cells (1000 μM) and the viability of the LLC-PK1 cells (400 μM) were not significantly (FIGS. 2A, 2B). The extents to which the viability of the two cell lines was lowered by the novel compound were dose dependent. The toxicity of the novel compound on these two cell lines was very low ($IC_{50}$ about 8 mM).

3.4.2 Novel Compound GMDTC Inhibits Cisplatin Cytotoxicity

Figure 3A:
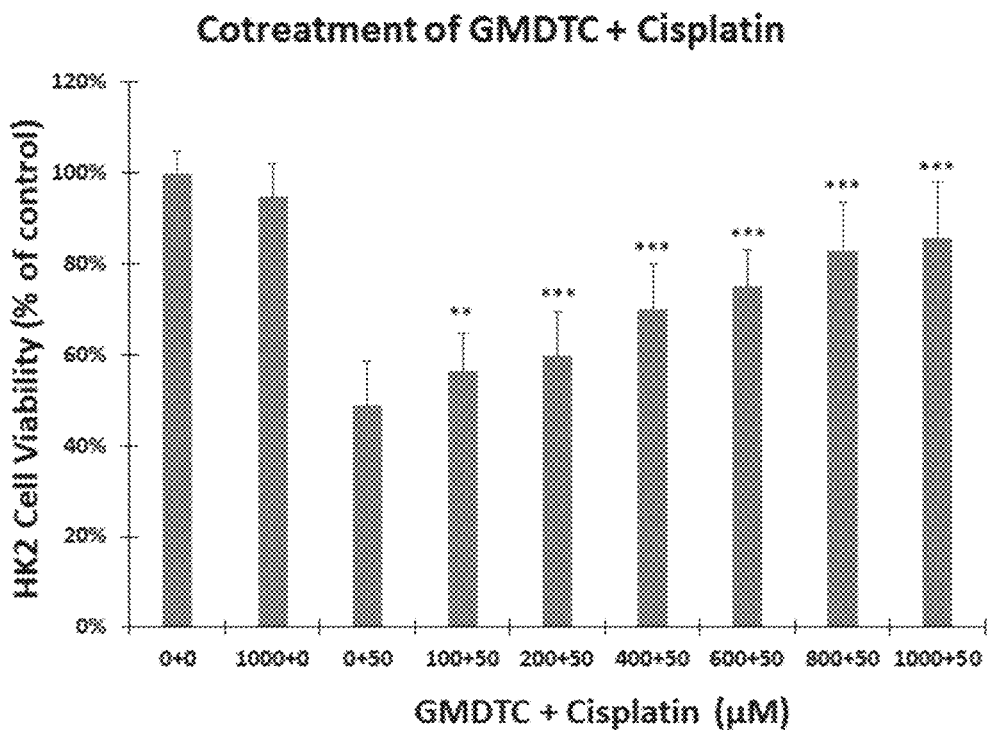
FIG. 3A shows the result of an in vitro cell viability assay of HK2 cells co-treated with various doses of GMDTC and 50 μM cisplatin for 24 h according to an example of the present disclosure.

The HK2 cells and the LLC-PK1 cells were treated with 50 μM cisplatin, 1000 μM novel compound, or 50 μM cisplatin+increasing doses of novel compound for 24 h. Toxicity was studied using an MTT cell viability assay. Both cells showed a 50% decrease in cell viability after cisplatin exposure. The novel compound could inhibit the cytotoxicity of cisplatin and increase cell viability to 80%. Cell viability was increased with increasing doses of the novel compound (see FIG. 3A).

Figure 3B:
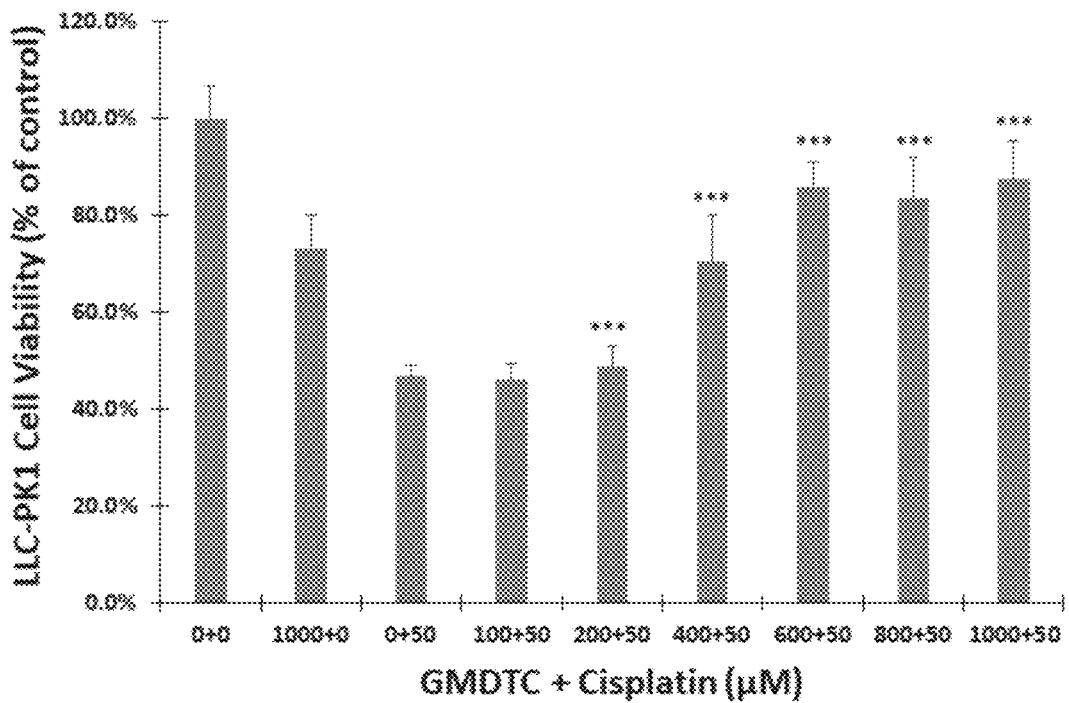
FIG. 3B shows the result of an in vitro cell viability assay of LLC-PK1 cells co-treated with various doses of GMDTC and 50 μM cisplatin for 24 h according to an example of the present disclosure.

As shown in FIG. 3B, the co-treatment could reduce cytotoxicity caused by both the novel compound and the cisplatin in an LLC-PK1 cell line assay.

3.4.3 Novel Compound GMDTC Attenuates Cisplatin Cytotoxicity in HK2 Cells.

Figure 4:
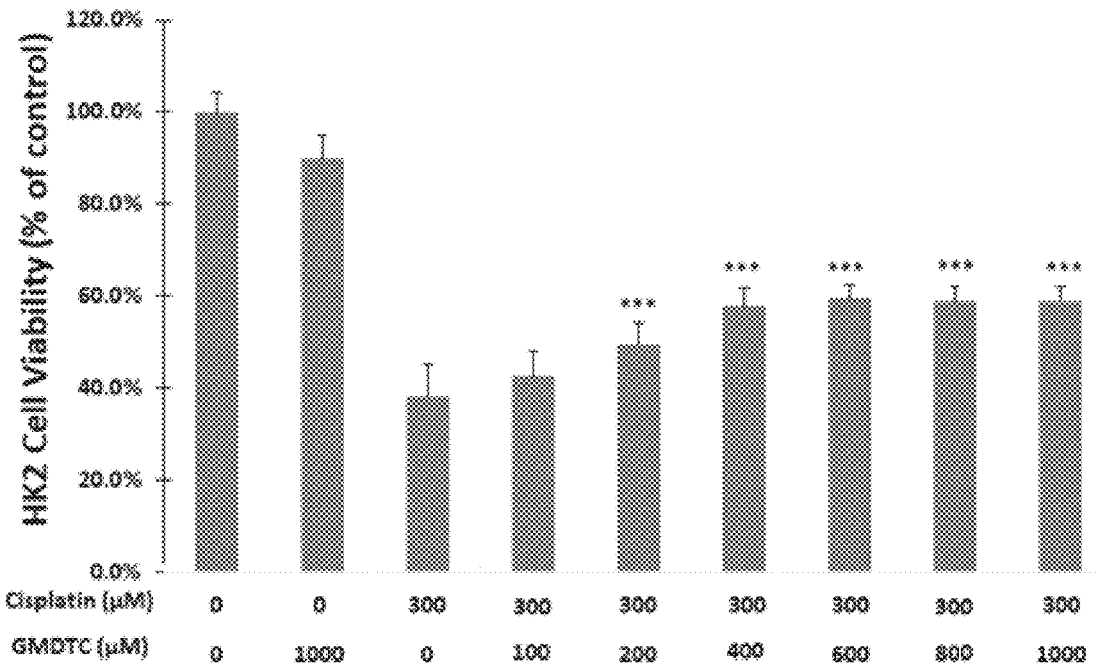
FIG. 4 shows the result of an in vitro cell viability assay of HK2 cells treated with 300 μM cisplatin for 30 min, medium removed & replaced, then treated with various doses of GMDTC for 24 hours according to an example of the present disclosure.

The HK2 cells were pretreated with 300 μM cisplatin for 30 min and washed twice with PBS. The medium was replaced, then the HK2 cells were treated with different concentrations of the novel compound for 48 h. The viability of the HK2 cells decreased to less than 40% of that of the control group. The damaged cells could be protected by the novel compound: following the addition of GMDTC, cell viability increased to 60% of that of the control group (see FIG. 4). The results indicate that the novel compound could effectively reduce cell damages caused by cisplatin.

3.4.4 Novel Compound Inhibits the Uptake of Cisplatin by HK2 Cells and Accelerates Platinum Clearance from Cells The amount of platinum in the cells was determined by an IPC-MS assay. When treated with 50 μM cisplatin, platinum concentration in HK2 cells was 202.6 ng/10⁶ cells; when co-administrated with 1000 μM novel compound, platinum concentration in HK2 cells drastically dropped by 91.5% to 17.2 ng/10⁶ cells.

After subjecting the HK2 cells to short-term exposure of cisplatin for 30 min, the HK2 cells were removed and cultured for 48 h. Platinum concentration was 8.33 ng/10⁶ cells. 48 hours after the administration of cisplatin, 1000 μM novel compound was added to the HK2 cells for intervention. Platinum concentration in the HK2 cells dropped by 38.0% to 5.16 ng/10⁶ cells as a result.

Figure 5A:
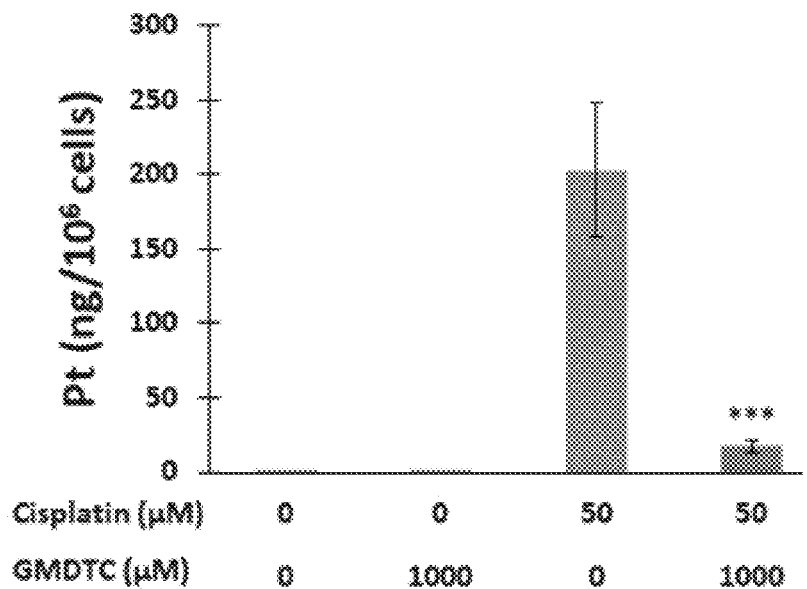
FIG. 5A shows the Pt content in HK2 cells co-treated with 1000 μM GMDTC and 50 μM cisplatin for 24 h in comparison to control cells and cells treated with 1000 μM GMDTC or 50 UM cisplatin respectively according to an example of the present disclosure.
Figure 5B:
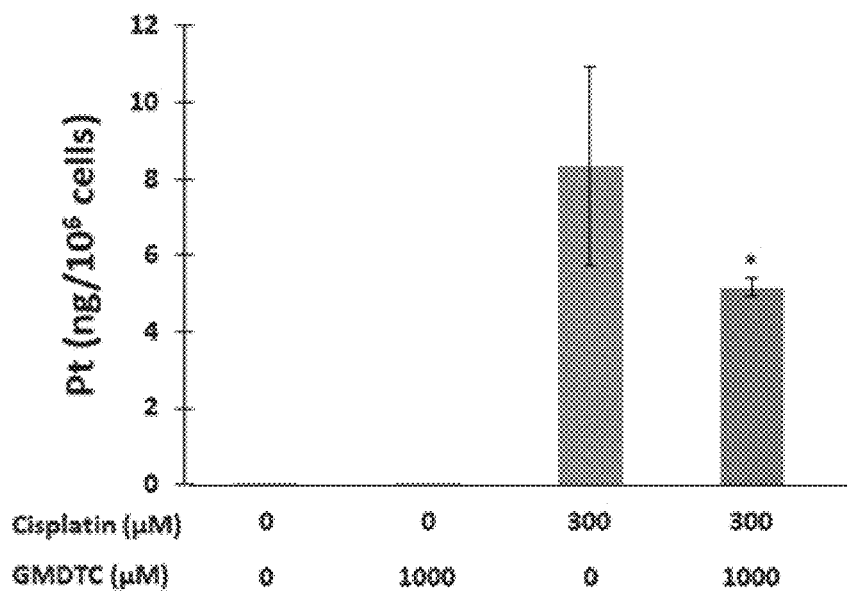
FIG. 5B shows the Pt content in HK2 cells when they were briefly exposed to 300 μM cisplatin for 30 min then removed and cultured for 48 h, and when the HK2 cells were rescued by 1000 μM GMDTC for 48 h after cisplatin treatment according to an example of the present disclosure.

The results are shown in FIGS. 5A and 5B. the novel compound could reduce cisplatin cytotoxicity by inhibiting cisplatin uptake of the HK2 cells. The novel compound could also accelerate the removal of platinum from the cells under the rescue action of the cells.

Example 4

This example determines the effect of the composition on a mouse tumor animal model.

4.1 Mouse 4T1 Breast Cancer Model

Female BALB/c mice (8 weeks old, weight 19-20 g) were selected from Charles River Laboratories. The mice were fed with a standard rodent diet and given ad libitum water. The animals were maintained in a 12-hour light/dark cycle, at constant temperature (20±1° C.) and humidity (50±5%). All animals were processed following protocols approved by the Animal Care and Use Committee.

4T1 breast cancer cells (1×10⁵) were subcutaneously injected into the right breasts of BALB/c mice. After injection, the mice were monitored for 10 days, then divided into 3 groups of six according to tumor size and body weight. Drug treatment started on day 11.

The control group was intraperitoneally (i.p.) administrated with 0.9% normal saline. The cisplatin treatment group was intraperitoneally administered with 5 mg/kg cisplatin twice a week. The experimental group (co-administration of cisplatin and the novel compound) was intraperitoneally injected with 5 mg/kg cisplatin twice a week and 500 mg/kg novel compound once a day; the novel compound was injected 2 h after the injection of cisplatin. All mice were treated for 3 weeks.

Tumor volume was estimated using the following formula: $V=\pi(a \times b^2)/6$, wherein a and b are the maximum and minimum diameters of the tumor, measured by a caliper. The body weights of the mice were monitored every 3-4 days during the experiment, and the mice were euthanized at the end of the treatment. After inhaling isoflurane for anesthesia, cardiac blood collection was performed as a termination procedure. In addition, the tumor, liver, kidney, adrenal gland, spleen, brain, lung and heart were taken out immediately after euthanization to record their weights. Subsequently, halves of the tissues are separated and immediately frozen in liquid nitrogen for future analysis, and the remaining halves were stored in 10% formalin for histopathological examination.

4.2 Testing Method: Blood Analysis Method

An EDTA tube was used to collect whole blood for a complete blood count (CBC) test. Plasma was collected by centrifugation blood collected in a heparin-coated tube. The plasma was used to carry out tests and analyses including CBC and a blood chemical test; plasma BUN and creatinine level were markers of kidney injury.

4.3 Testing Method: Histopathological Method

Histopathological examination of mouse tissues: histopathological changes of the kidney were examined by a 4 μm-thick deparaffinized section stained with hematoxylin and eosin (HE). To evaluate tubular damages, dilation, necrosis, apoptosis, and cast formation of renal tubules were assessed via 10 different fields of view (Zeiss Axio imager electrofluorescence microscope) at the cortical medullary junction of the kidney.

4.4 Testing Method: Method for Determining Platinum Distribution in Tissues

The kidney was sliced, weighed and dissolved in 70% $HNO_3$; blood plasma was diluted with 70% $HNO_3$. The sample was heated by a 100° C. hot block until thoroughly evaporated. All solid residues were re-dissolved in 5 mL of 2% $HNO_3$. Platinum was quantified by inductively coupled plasma mass spectrometry (ICP-MS).

Figure 6A:
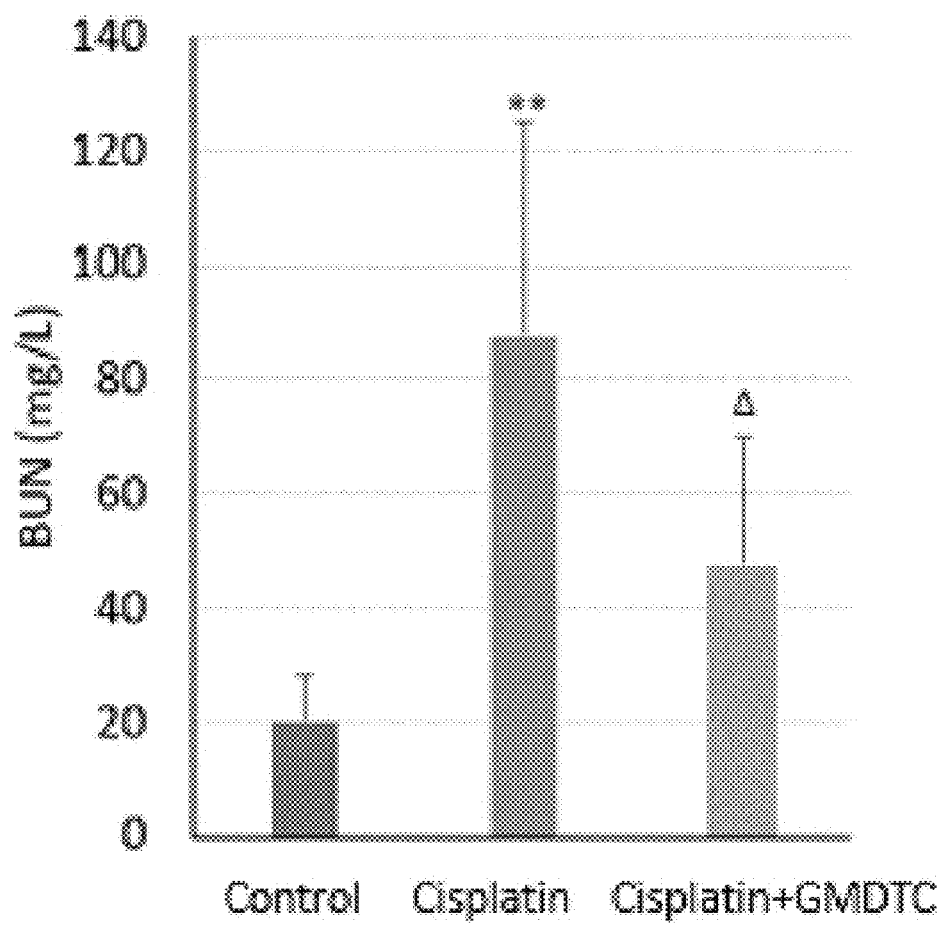
FIG. 6A shows blood BUN level in mice of Control (blue), Cisplatin treated (orange) and Cisplatin-GMDTC co-treatment (gray) groups according to an example of the present disclosure.
Figure 6B:
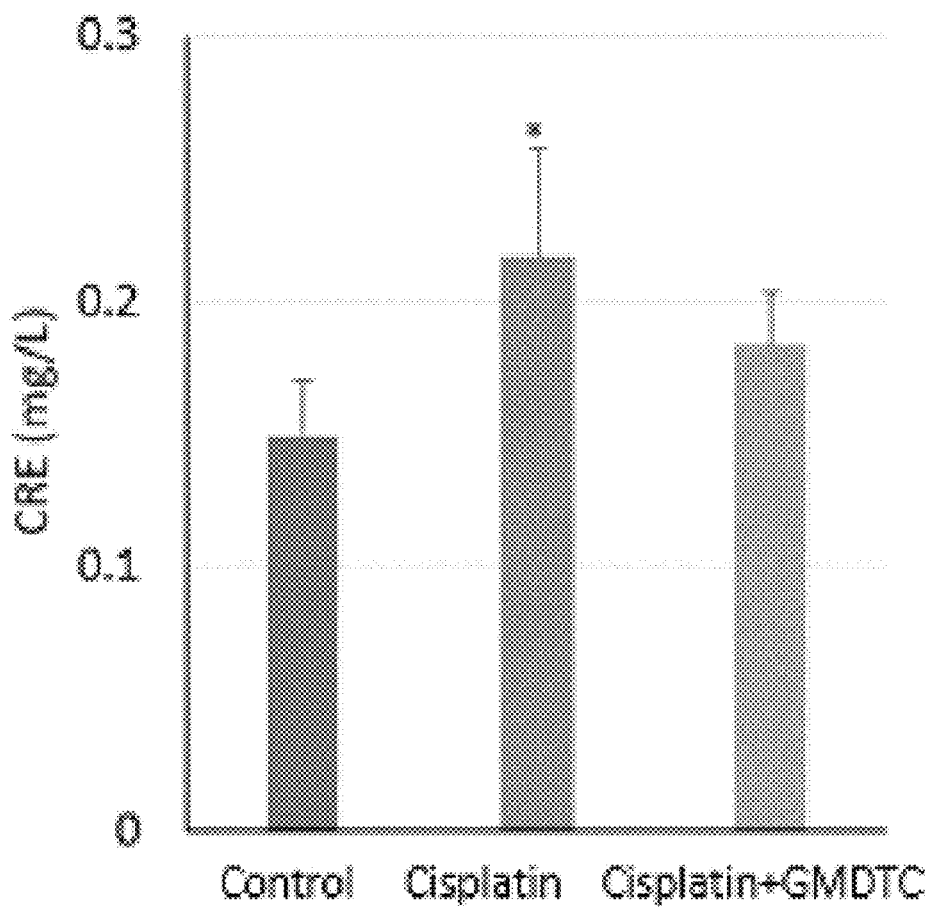
FIG. 6B shows blood CRE level in mice of Control (blue), Cisplatin treated (orange) and Cisplatin-GMDTC co-treatment (gray) groups according to an example of the present disclosure.
Figure 7A:
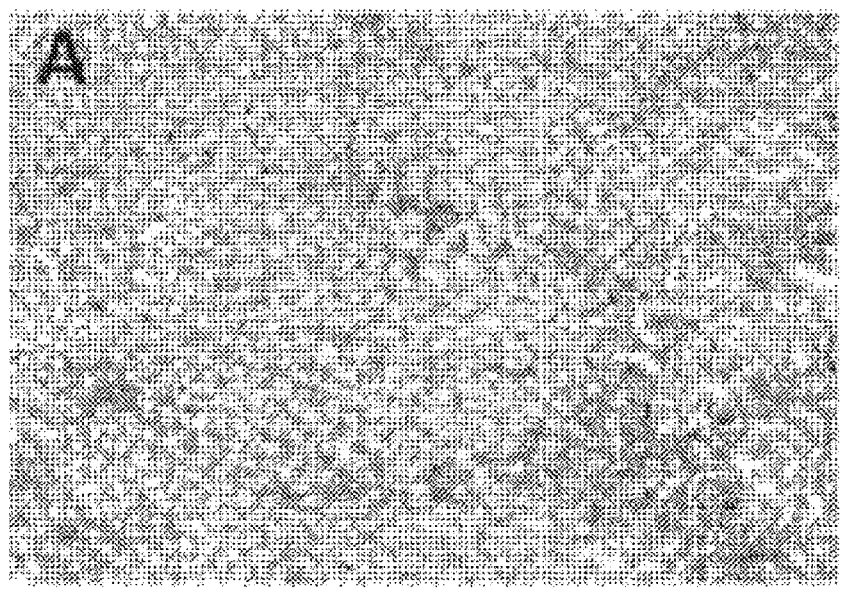
FIG. 7A shows histopathological sections of a kidney in mice treated with vehicle showing a zone of normal tubule cells in the outer medullary stripe extending into the cortex, the normal glomeruli (Δ), and renal tubules lined by tubular cells (↑) (scale bar: 100 μm) according to an example of the present disclosure.
Figure 7B:
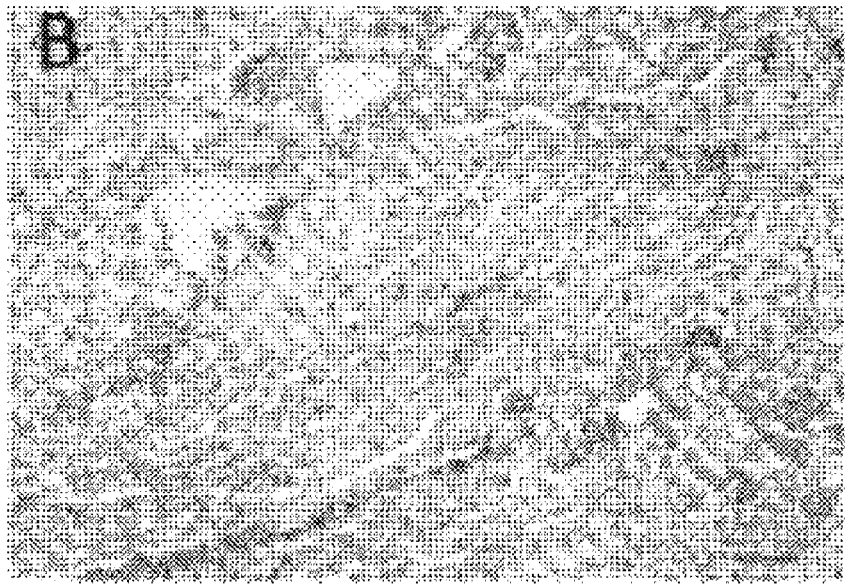
FIG. 7B shows histopathological sections of a kidney in mice treated with Cisplatin showing a zone of extensive necrosis and degeneration of tubule cells in the outer medullary stripe extending into the cortex, the renal tubules dilatation or vacuolation (*), necrotic tubular cells (↑), necrotic glomeruli (Δ) (scale bar: 100 μm) according to an example of the present disclosure.
Figure 7C:
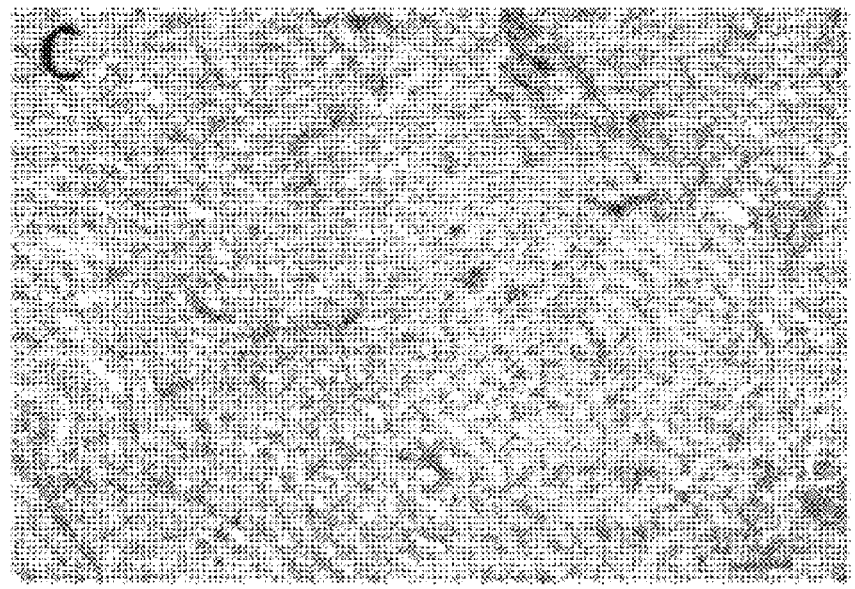
FIG. 7C shows histopathological sections of a kidney in mice co-treated with Cisplatin and GMDTC with no abnormalities. (scale bar: 100 μm) according to an example of the present disclosure.
Figure 7D:
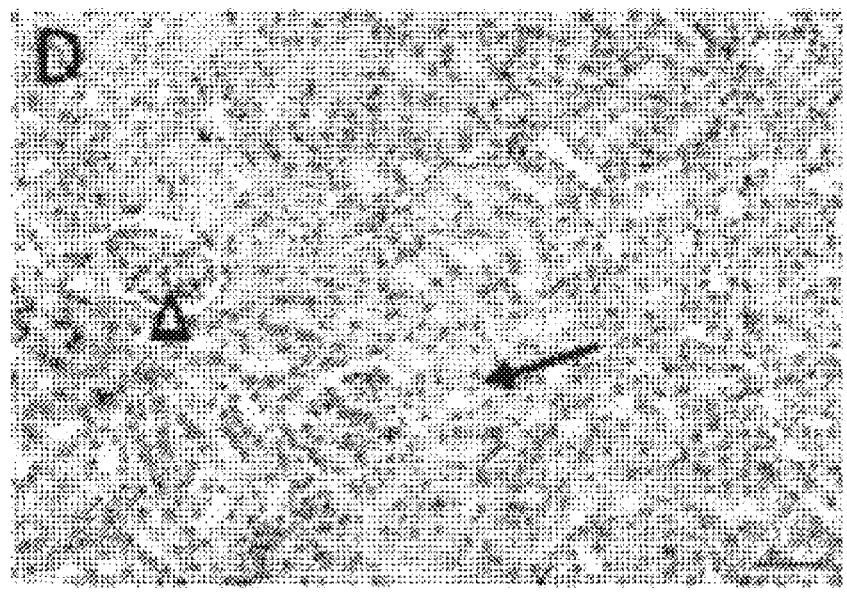
FIG. 7D shows histopathological sections of a kidney in mice treated with vehicle showing a zone of normal tubule cells in the outer medullary stripe extending into the cortex, the normal glomeruli (Δ), and renal tubules lined by tubular cells (↑) (scale bar: 50 μm) according to an example of the present disclosure.
Figure 7E:
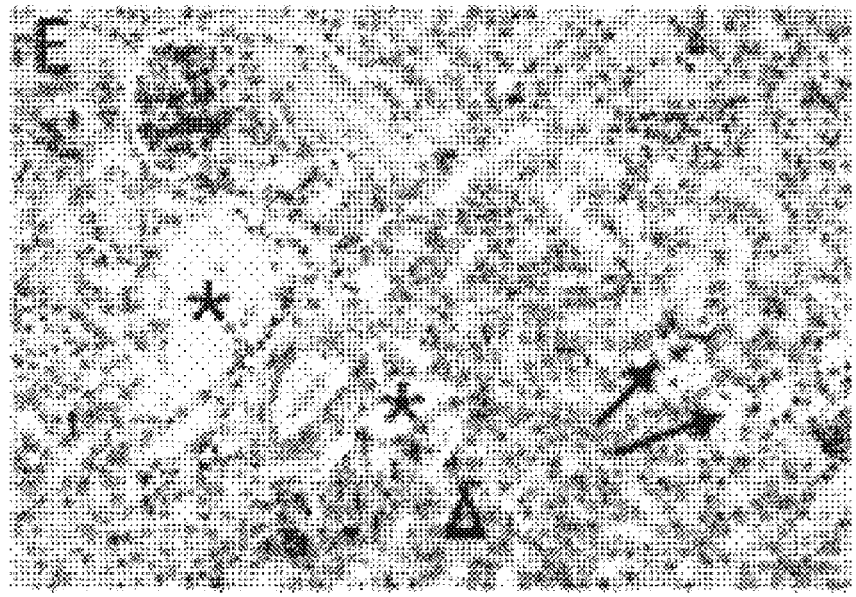
FIG. 7E shows histopathological sections of a kidney in mice treated with Cisplatin showing a zone of extensive necrosis and degeneration of tubule cells in the outer medullary stripe extending into the cortex, the renal tubules dilatation or vacuolation (*), necrotic tubular cells (↑), necrotic glomeruli (Δ) (scale bar: 50 μm) according to an example of the present disclosure.
Figure 7F:
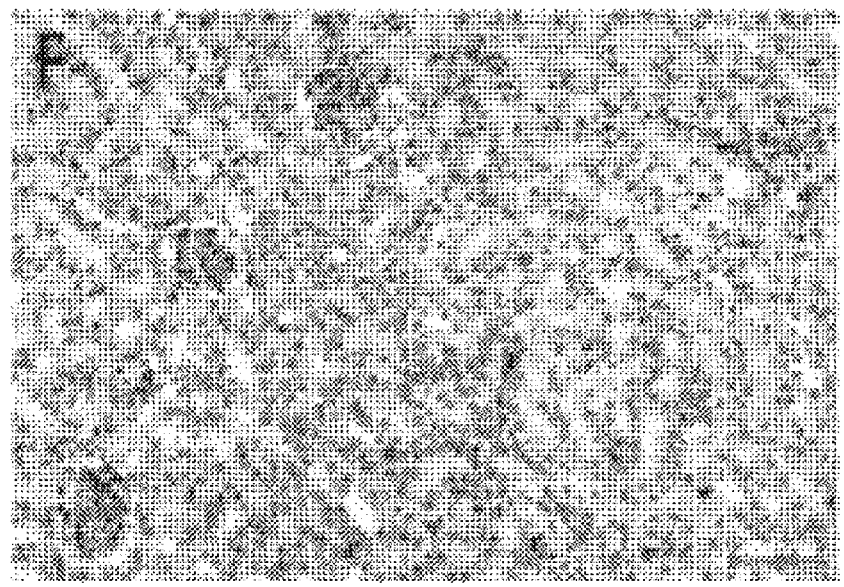
FIG. 7F shows histopathological sections of a kidney in mice co-treated with Cisplatin and GMDTC with no abnormalities. (scale bar: 50 μm) according to an example of the present disclosure.

4.5 Experimental Results 4.5.1 the Inhibition of Novel Compound GMDTC on Cisplatin-Induced Toxic Renal Damage A 4T1 breast cancer mouse model was used to evaluate the antitumor ability and protective effect of the novel compound. As shown in FIGS. 6A and 6B, 5 mg/kg cisplatin was administered twice a week. In the novel compound group, 500 mg/kg novel compound was administrated 2 h after cisplatin administration. Three weeks later, the average BUN level of the mice administrated with cisplatin was 87.9 mg/dl, which was 4 times that of the control group. When the novel compound was used for intervention, BUN level dropped by 46% to 47.6 mg/dl. Testing the CRE level gave similar results.

As shown in the results gathered from pathological sections of the kidney (FIGS. 7A-F), the mice in the cisplatin group showed extensive necrosis and degeneration area on cells from the lateral medulla to the cortical tubules. On the other hand, there was no significant difference between the novel compound intervention group and the control group.

4.5.2 the Inhibition of Novel Compound GMDTC on Cisplatin-Induced Ototoxicity

Figure 11:
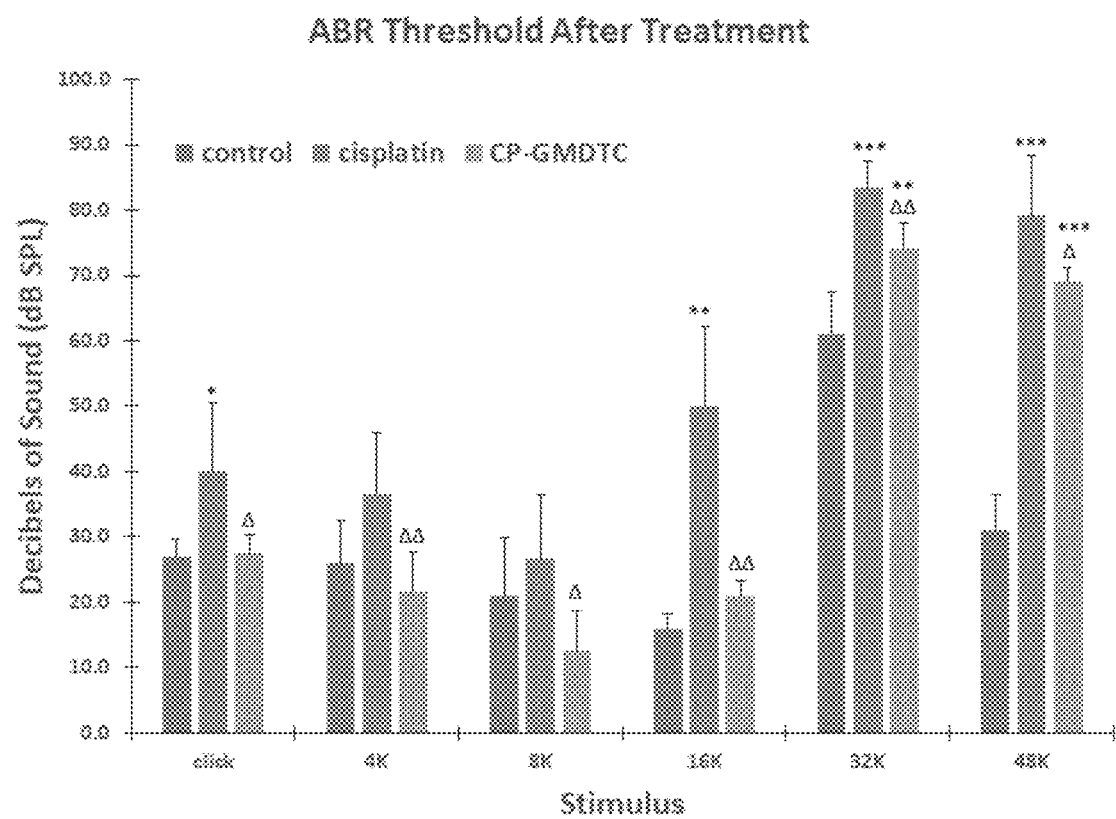
FIG. 11 shows the auditory brainstem response (ABR) thresholds (decibels of sound pressure level, dB SPL) in mice of Control (blue), Cisplatin (orange) and Cisplatin-GMDTC co-treatment (gray) groups according to an example of the present disclosure.

As shown in FIG. 11, the auditory brainstem response (ABR) is an auditory evoked potential extracted from ongoing electrical activity in the brain and recorded via electrodes placed on the scalp. The measured recording is a series of six to seven vertex positive waves of which I through V are evaluated. Here, the ABR is used for auditory threshold estimation as a representation of hearing. After 3 weeks of cisplatin therapy and GMDTC rescue treatment, the mice of the Cisplatin group showed higher ABR thresholds at click stimulus and at tones stimuli (4, 8, 16, 32, and 48 kHz) when compared to mice of Control group. The mice of Cisplatin-GMDTC co-treatment group showed lower ABR thresholds at click stimulus and at tones stimuli when compared to mice of Cisplatin group.

Figure 12:
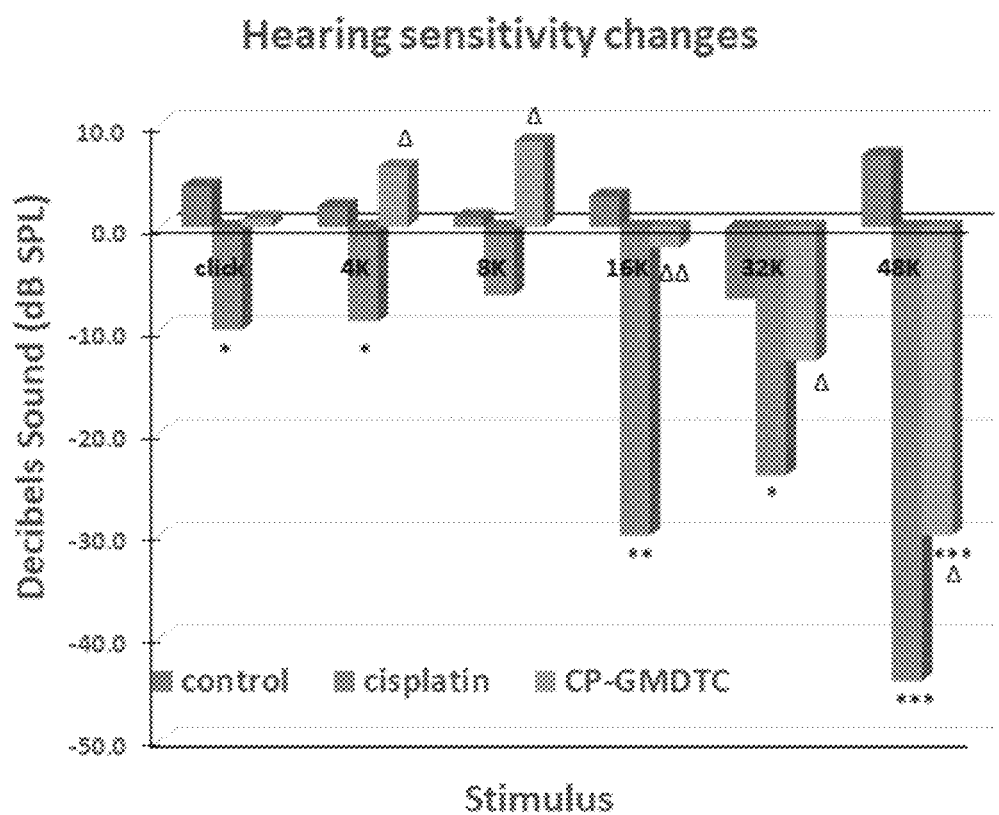
FIG. 12 shows the changes of hearing sensitivity of the deducting the ABR thresholds before and after treatment in mice of Control (blue), Cisplatin (orange) and Cisplatin-GMDTC co-treatment (gray) groups (<0 means decrease sensitivity, >0 means increase sensitivity) according to an example of the present disclosure.

As shown in FIG. 12, the changes in hearing sensitivity were measured by deducting the ABR thresholds before and after treatment (<0 means decrease sensitivity, >0 means increase sensitivity). Control mice showed very little changes during the treatment. The mice of Cisplatin group showed decreased hearing sensitivity at all stimuli especially in the high-frequency range (16-48 kHz). The mice of co-treatment group showed small changes at click stimulus and lower frequency tones stimuli (4-16 kHz), and decreased hearing sensitivity at high frequency (32-48 kHz).

4.5.3 Antitumor Activity Assay of Cisplatin+Novel Compound GMDTC

Figure 8:
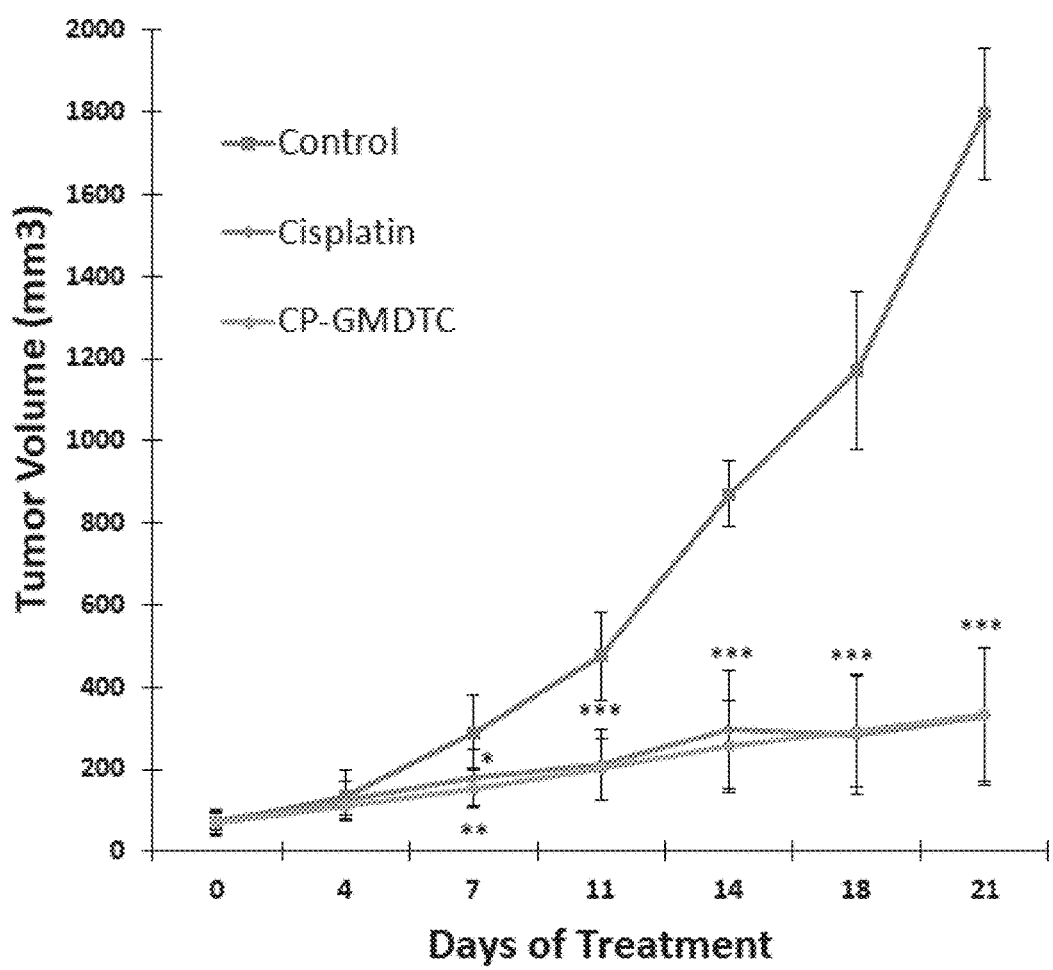
FIG. 8 shows tumor growth curve in a 4T1 breast cancer mice model during Cisplatin and GMDTC treatment [mice of Control (blue), Cisplatin (orange) and Cisplatin-GMDTC co-treatment (gray) groups] according to an example of the present disclosure.
Figure 9:
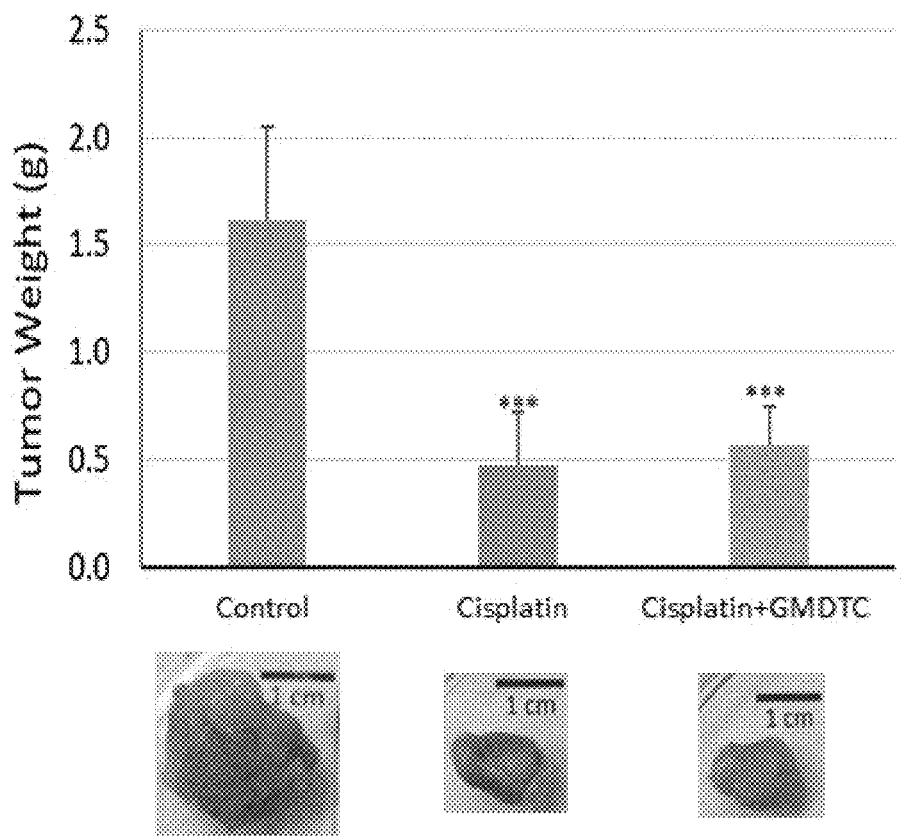
FIG. 9 shows tumor weight measurement results in the 4T1 mouse model after a course of treatment according to an example of the present disclosure.

Through assaying tumor-related indicators, cisplatin+novel compound GMDTC does not reduce antitumor activity compared with using cisplatin alone (FIG. 8). The measurements of tumor growth and final tumor size after administration showed that the cisplatin+novel compound co-treatment group significantly inhibits tumor growth and metastasis compared with the control group (FIG. 9).

4.5.4 Influence of the Novel Compound on Regular Metal Content in the Body

Other essential metals in the mice are also analyzed by ICP-MS (Table 1). Compared with the control mice, the novel compound does not affect the amount and distribution of normal metals (such as $Zn^{2+}$, $Mg^{2+}$, $Al^{3+}$, $Mn^{2+}$ and $Cu^{2+}$) in the body. Please refer to Table 1 and Table 2.

TABLE 1

Amount of regular metals in kidney (μg/g) after administration of cisplatin and GMDTC

|  | 24Mn | 27Al | 55Mn | 65Cu | 66Zn | 195Pt |
|---|---|---|---|---|---|---|
| Control | 236.5 | 4.22 | 1.04 | 4.73 | 23.6 | 0.015 |
| Cisplatin | 237.8 | 3.93 | 0.92 | 4.13 | 24.4 | 9.841 |
| CP + GMDTC | 253.1 | 6.78 | 1.09 | 5.96 | 31.3 | 7.347 |

TABLE 2

Amount of regular metals in plasma (μg/ml) after administration of cisplatin and GMDTC

|  | 24Mn | 27Al | 55Mn | 65Cu | 66Zn | 195Pt |
|---|---|---|---|---|---|---|
| Control | 35.7 | 3.60 | 0.009 | 1.33 | 1.27 | 0.001 |
| Cisplatin | 28.7 | 5.23 | 0.010 | 1.57 | 0.90 | 0.175 |
| CP + GMDTC | 24.8 | 3.60 | 0.010 | 1.66 | 0.76 | 0.124 |

In summary, the present disclosure provides a composition prepared from a platinum-based antitumor compound and a novel compound, wherein the novel compound is sodium (S)-2-(dithiocarboxylate ((2S,3R,4R,5R)-2,3,4,5,6-pentahydroxyhexyl)amino)-4-(methylthio)butyrate. The present disclosure also provides an application for the aforementioned composition as an antitumor drug. It can be determined by experiments that the novel compound in the composition can effectively chelate the heavy metal in the platinum-based antitumor compound. As a result, the various adverse reactions when the platinum-based compound is used alone can be effectively inhibited, the dosage of the platinum-based antitumor compound can be increased, and the antitumor effect is optimized. Also, the novel compound is non-toxic and cannot chelate the essential metals in the human body, therefore it would not impose adverse effects on the human body. The composition and its application as an antitumor drug provided by the present disclosure solve the technical defects of platinum-based antitumor drugs of the prior art, namely severe adverse effects and the development of drug resistance during the administration of platinum-based antitumor drugs.

The above only demonstrates some preferred examples of the present disclosure. It should be pointed out that for the person skilled in the art, without departing from the principle of the present disclosure, several improvements and modifications can be made, and these improvements and modifications should be regarded as falling within the protection scope of the present disclosure.

What is claimed is:

1. A method of treating solid tumors in a subject suffering from cancer, including:
    administering a drug to the subject, wherein the drug comprises, in parts by mole, 1-5 parts of a platinum-based antitumor compound and 1-50 parts of sodium (S)-2-(dithiocarboxylate ((2S,3R,4R),5R)-2,3,4,5,6-pentahydroxyhexyl)amino)-4-(methylthio)butyrate (GMDTC).

2. The method according to claim 1, wherein the platinum-based antitumor compound is one or more selected from the group consisting of cisplatin, oxaliplatin, and carboplatin.

3. The method according to claim 2, wherein the platinum-based antitumor compound is cisplatin.

4. The method according to claim 1, wherein the drug comprises, in parts by mole, 1-3 parts of the platinum-based antitumor compound and 1-20 parts of GMDTC.

5. The method according to claim 4, wherein the drug comprises, in parts by mole, 1 part of the platinum-based antitumor compound and 20 parts of GMDTC.

6. The method according to claim 1, wherein GMDTC is administered 2 hours after administration of cisplatin.

7. The method according to claim 1, wherein the cancer is breast cancer.

\* \* \* \* \*